US010130561B2

(12) United States Patent
Karlinsey

(10) Patent No.: US 10,130,561 B2
(45) Date of Patent: *Nov. 20, 2018

(54) FUNCTIONALIZED CALCIUM PHOSPHATE HYBRID SYSTEMS FOR CONFECTIONERY AND FOODSTUFF APPLICATIONS

(76) Inventor: Robert L. Karlinsey, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/507,989

(22) Filed: Jul. 23, 2009

(65) Prior Publication Data
US 2011/0020245 A1   Jan. 27, 2011

Related U.S. Application Data

(63) Continuation-in-part of application No. 11/701,210, filed on Jan. 31, 2007, now abandoned.

(60) Provisional application No. 60/763,607, filed on Jan. 31, 2006.

(51) Int. Cl.
A61K 6/033 (2006.01)

(52) U.S. Cl.
CPC .................... A61K 6/033 (2013.01)

(58) Field of Classification Search
USPC ...................... 424/49, 52; 427/2.1
See application file for complete search history.

(56) References Cited

U.S. PATENT DOCUMENTS

| | | | |
|---|---|---|---|
| 3,190,568 A | 6/1965 | Freedman et al. | |
| 3,876,160 A | 4/1975 | Bloch | |
| 4,018,619 A | 4/1977 | Webster et al. | |
| 4,677,140 A | 6/1987 | Shioitsu | |
| 5,053,212 A | 10/1991 | Constantz et al. | |
| 5,342,441 A | 8/1994 | Mandai et al. | |
| 5,833,954 A * | 11/1998 | Chow et al. | 424/49 |
| 6,053,970 A | 4/2000 | Ison et al. | |
| 6,126,097 A | 10/2000 | Chen et al. | |
| 6,334,583 B1 * | 1/2002 | Li | B02C 17/08 241/175 |
| 6,840,961 B2 | 1/2005 | Tofighi et al. | |
| 2002/0037258 A1 | 3/2002 | Dodd et al. | |
| 2003/0069638 A1 | 4/2003 | Barlow et al. | |
| 2003/0120351 A1 | 6/2003 | Tofighi et al. | |
| 2003/0124006 A1 | 7/2003 | Dixon, Jr. et al. | |
| 2003/0199615 A1 * | 10/2003 | Chaput | A61K 9/0024 524/2 |
| 2004/0101494 A1 | 5/2004 | Scott et al. | |
| 2004/0126335 A1 | 7/2004 | Faller et al. | |
| 2005/0025721 A1 | 2/2005 | Holme et al. | |
| 2005/0084461 A1 | 4/2005 | Winston et al. | |
| 2005/0241535 A1 | 11/2005 | Bohner | |
| 2006/0034975 A1 * | 2/2006 | Schechner | A23G 3/0085 426/3 |
| 2006/0175443 A1 | 8/2006 | Bysouth | |
| 2006/0270752 A1 | 11/2006 | Xu et al. | |
| 2006/0292200 A1 * | 12/2006 | Delaney | A61K 33/42 424/423 |
| 2007/0059379 A1 | 3/2007 | Gerber | |
| 2007/0149650 A1 | 6/2007 | Masuda | |
| 2007/0178220 A1 * | 8/2007 | Karlinsey | 427/2.1 |
| 2007/0183984 A1 | 8/2007 | Haas et al. | |
| 2008/0187500 A1 * | 8/2008 | Karlinsey | 424/52 |
| 2008/0221681 A1 | 9/2008 | Trieu et al. | |
| 2009/0324516 A1 | 12/2009 | Muscle et al. | |
| 2010/0291164 A1 | 11/2010 | Karlinsey | |

FOREIGN PATENT DOCUMENTS

| | | | |
|---|---|---|---|
| CA | 1089428 | 11/1980 | |
| FR | 2594130 | 8/1987 | |
| GB | 593777 | 10/1947 | |
| GB | 593777 | 10/2007 | |
| JP | 05085709 | * 4/1993 | .......... C01B 25/455 |
| JP | 2000245821 | 9/2000 | |
| JP | 2003073182 | 3/2003 | |
| JP | 2003093496 | 4/2003 | |
| WO | 4877603 | 10/1989 | |
| WO | WO-4877603 | 10/1989 | |
| WO | 9840406 | 9/1998 | |
| WO | 20020037258 | 3/2002 | |

(Continued)

OTHER PUBLICATIONS

Karlinsey et al., "Solid-state preparation and dental application of an organically modified calcium phosphate." J Mater Sci (2009) 44 :346-349. (Year: 2008).*

Dushkin, "Potential of Mechanochemical Technology in Organic Synthesis and Synthesis of New Materials", Institute of Solid State Chemistry and Mechanochemistry, Siberian Branch of the Russian Academy of Sciences, Ul. (Russia) Chemistry for Sustainable Development, vol. 12, 2004, pp. 251-273, XP002728802, http://www.sibran.ru/upload/iblock/4a3/4a30bb11b1f14.

Kim, et al., "Bioactive Organic-Inorganic Composite Prepared by Mechanochemical Method", Key Engineering Materials, Trans Tech Publications Ltd., Stafa-Zurich, CH, vol. 218-220, No. Bioceramics-14, Jan. 1, 2002, pp. 295-298, XP009127712, ISSN: 1013-9826, p. 296.

(Continued)

Primary Examiner — Walter E Webb
(74) Attorney, Agent, or Firm — C. John Brannon; Brannon Sowers & Cracraft PC

(57) ABSTRACT

A method for repairing dentition, including milling beta tricalcium phosphate with sufficiently high energy to substantially distressed its lattice structure, mechanochemically chelating an edible acid thereto to yield functionalized calcium phosphate moieties, and incorporating the functionalized calcium phosphate moieties into an edible material to yield a calcium phosphate delivery system. The calcium phosphate delivery system is introduced into an oral environment and dentition is repaired. The functionalized calcium phosphate moiety is characterized by weakly bonded fumaric acid at least partially wrapped around distressed calcium phosphate particles, and dentition repair occurs at a dentition depth of at least 10 microns below the surface.

11 Claims, 8 Drawing Sheets

(56) References Cited

FOREIGN PATENT DOCUMENTS

WO  WO-20020037258  3/2002
WO  2007068062  6/2007

OTHER PUBLICATIONS

Schemehorn, et al., "Comparison of Fluoride Uptake into Tooth Enamel from Two Fluoride Varnishes Containing Different Calcium Phosphate Sources", The Journal of Clinical Dentistry, vol. 22, No. 2, 2011, pp. 51-54, http://premusa.com/Downloadablefiles/JCD_22_2_Schemehorn_et-al.pdf; entire document.
Walsh, "Evidence that demands a verdict: latest developments in remineralization therapies", Australasian Dental Practice, 2009, pp. 49-59, http://geriatricdentistry.com/wp/wp-content/uploads/2011/08/L.-Walsh-remin.article.pdf; p. 50, col. 2, paragraph 2; p. 51, col. 2, paragraphs2-3, col. 3, paragraph 1.
Busch, "Regeneration of Human Tooth Enamel", Angewandte Chemie International Edition 2004:43(11); 1428-1431.

\* cited by examiner

FUNCTIONALIZED CALCIUM PHOSPHATE HYBRID SYSTEMS FOR CONFECTIONERY AND FOODSTUFF APPLICATIONS

CROSS-REFERENCE TO RELATED APPLICATIONS

This application is a continuation-in-part of, and claims priority to, utility patent application Ser. No. 11/701,210 filed Jan. 31, 2007 and published as U.S. Patent Pub. No. 2007/0178220, which claimed the benefit of priority to U.S. provisional patent application Ser. No. 60/763,607, filed on Jan. 31, 2006.

TECHNICAL FIELD

The present novel technology relates generally to the application of functionalized calcium-releasing hybrid moieties to mints, candies, gums, lozenges, and other confectionery or foodstuff formats, as well as to flosses, brushes and the like, to provide improved therapeutic and cosmetic dental benefits.

BACKGROUND

Preventing caries and cavities and improving the delivery of minerals that contribute to healthy teeth are important goals in oral health care. While preventive products can be extremely effective, sometimes the action of these products cannot keep up with consumer/patient habits. Many consumers are simply lax in oral health care, preferring diets rich in sweet foods over regular oral health care exercises. Likewise, the replacement of sugared products with sugar free products (such as gums, lozenges, and mints) has been an effective step for saliva stimulation after or between meals, which can effectively assist in the remineralization of teeth. Although the stimulated saliva is effective, there exist other opportunities to further improve dental health through the supplemental delivery of calcium and phosphate to the dentition.

While many drinks and other comestibles are currently fortified with calcium, the calcium is typically added in the form of a highly soluble precursor, such as calcium gluconate, calcium lactate or the like. While such highly soluble calcium is advantageous for quick and efficient absorption through the stomach and intestines, such rapid dissolution is less desirable for a calcium supplement intended to reside in the mouth for sufficient time to promote remineralization of the teeth. For such remineralization a relatively slow and steady calcium supply is more desirable. Tricalcium phosphate is a cheap, plentiful and rich calcium source with a very slow calcium release rate. Unfortunately, conventional calcium phosphate materials dissolve too slowly and such technologies are only marginally effective in providing useful quantities of minerals to the teeth.

Thus, there remains a need for mineral delivery compounds that can help boost remineralization efficacy through confectionery and foodstuff formats, such as a mint, gum, or lozenge. The present novel technology discussed herein addresses this need.

SUMMARY

The present novel technology relates generally to the inclusion of functionalized calcium-releasing hybrid moieties to mints, candies, gums, lozenges, and other confectionery and foodstuff formats in to order boost remineralization efficacy of the dentition, as well as to potentially provide cosmetically-important whitening of the enamel.

One object of the present novel technology is to provide an improved comestible including functionalized calcium-releasing hybrid moieties for the purposes of delivering useful minerals to teeth through formats including mints, gums, and other confectioneries/foodstuffs. Further objects, features, and advantages will become apparent from a consideration of the following description.

DETAILED DESCRIPTION

Figure 1:
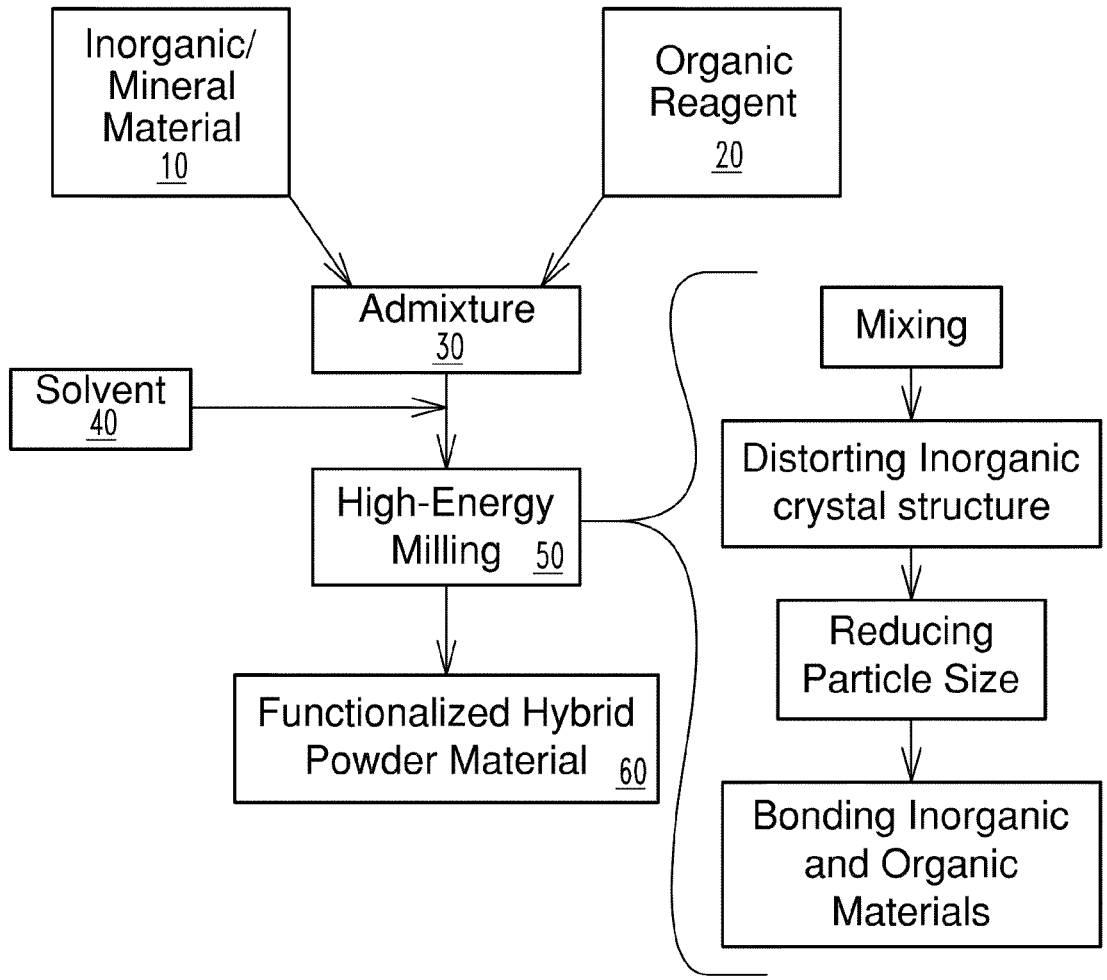
FIG. 1 is a flow chart representing a process for producing functionalized moieties according to the present novel technology.

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

The present novel technology relates to comestibles containing calcium-releasing functionalized hybrid moieties, wherein sufficient quantities of calcium and/or other predetermined minerals are released at a predetermined rate sufficient to assist in the remineralization of teeth during the duration of the comestible residing in the mouth. The present novel technology also relates to a method for producing a thermodynamically and kinetically stable material that releases ions and moieties, such as calcium, at a predetermined and controllable rate due to the complex chemistry created during the alloying process. This technique was developed in part to address a need for, among other things, improved mints, gums, lozenges, and other confectionery and foodstuff formats. Accordingly, the following examples and embodiments tend to reflect and relate to chemistries having dental applications. However, the present novel technology is broadly applicable beyond the specific dental applications discussed herein.

One aspect of the present novel technology relates to the application of calcium-releasing functionalized hybrid materials that may provide improved dental benefits to consumers by delivering small, surfactant-coated minerals to a substrate, such as dentition. The functionalized surface aids in promoting direct contact between a target material (such as the pellicle, enamel, or the like), and therefore allows for more efficient delivery of a desired mineral component (such as calcium and phosphate).

In one specific aspect of the present novel technology, the novel chemical synthesis method detailed herein below exploits a high-energy mechanochemical ball milling process to produce a relatively large amount of relatively inexpensive functionalized complexes. Typically, the functionalized complexes are blends of independent organic and inorganic reagents coupled together to yield a hybrid material with predetermined physical and chemical properties. A typical inorganic reagent may include a calcium phosphate mineral, such as calcium phosphate tribasic, calcium phosphate dibasic, dicalcium phosphate, or the like. Alternatively, other inorganic materials may include sodium, magnesium, iron, silicon, aluminum, manganese, titanium and the like in various mineralogical forms (such as oxides, phosphates, carbonates, nitrides and the like).

Typical organic reagents may include edible acids, anionic surfactants, cationic surfactants, neutral surfactants, polyethers or polyesters, polymethyl methacrylate, or the like. Other commonly selected organic reagents may include those materials with properties akin to those species listed above.

For example, hybrid calcium phosphate-fumaric acid systems may be produced in various formulations for improving remineralization efficacy of a mint, candy, gum, lozenge, or the like. The hybrid synthesis process is described below.

Hybrid Synthesis

The preparation of organic-inorganic materials via a mechanochemical process is illustrated in FIG. 1 and described as follows. Depending upon the desired composition, the mixture may range from between about 0.5 and 99.5 weight percent inorganic precursor material, with the balance being organic precursor material. In this example of functionalized moiety synthesis, the inorganic starting material 10 is tricalcium phosphate and the organic starting material 20 is fumaric acid; however, any convenient inorganic and organic precursors 10, 20 may be selected. Tricalcium phosphate (TCP, $Ca_3(PO_4)_2$) 10 plus fumaric acid (FA) 20 may be combined to define an admixture 30. The admixture 30 is typically added to a vessel containing a plurality of milling media balls, such as ten 20 millimeter diameter balls. The admixture 30 typically contains between about 0.1 and 30 weight percent FA 20 with the balance substantially TCP 10, more typically contains between about 1 and about 20 weight percent FA 20, and still more typically about 10 weight percent FA 20. Additionally, a small amount of an organic solvent 40, such as pentane, may be added as a milling facilitator. Once loaded with the admixture 30 and milling media, the vessel is typically locked onto the sun wheel of a planetary ball mill. The vessel is then rotated unidirectionally and opposite the rotational direction of the sun wheel at a sufficiently high speed for a duration of time (high-energy milling 50) sufficient to yield functionalized chemical moieties, such as, for example, at least about 400 rpm for about two hours. At the end of the milling process 50 the resulting powder 60 is substantially composed of functionalized moieties.

Figure 2A:
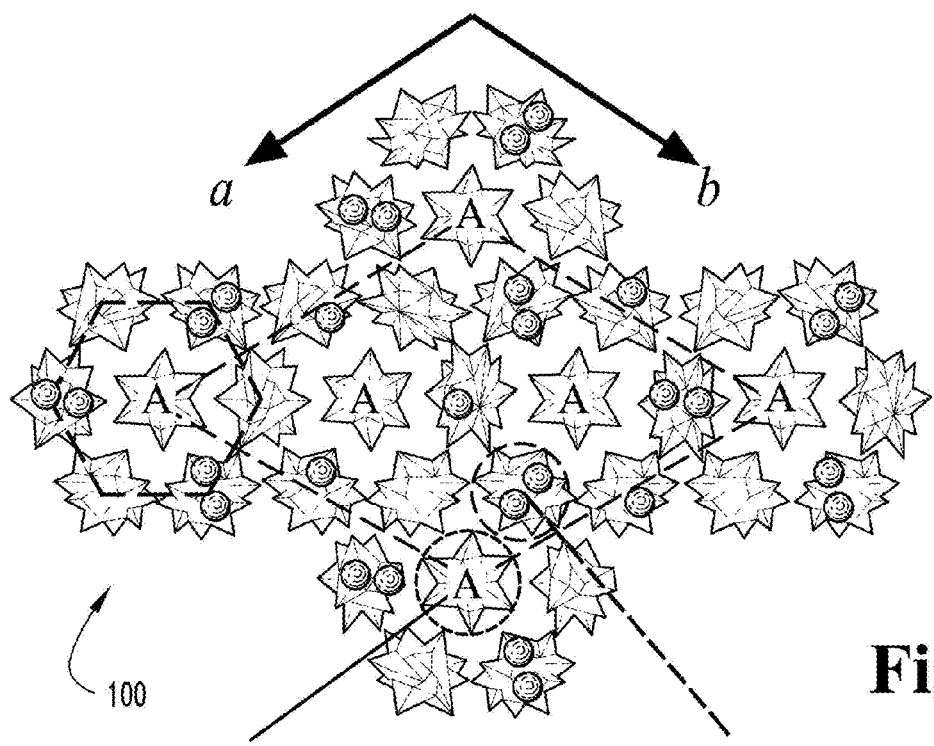
FIG. 2 is a schematic representation of a distressed and functionalized calcium phosphate structure according to a first embodiment of the present novel technology.
Figure 2B:
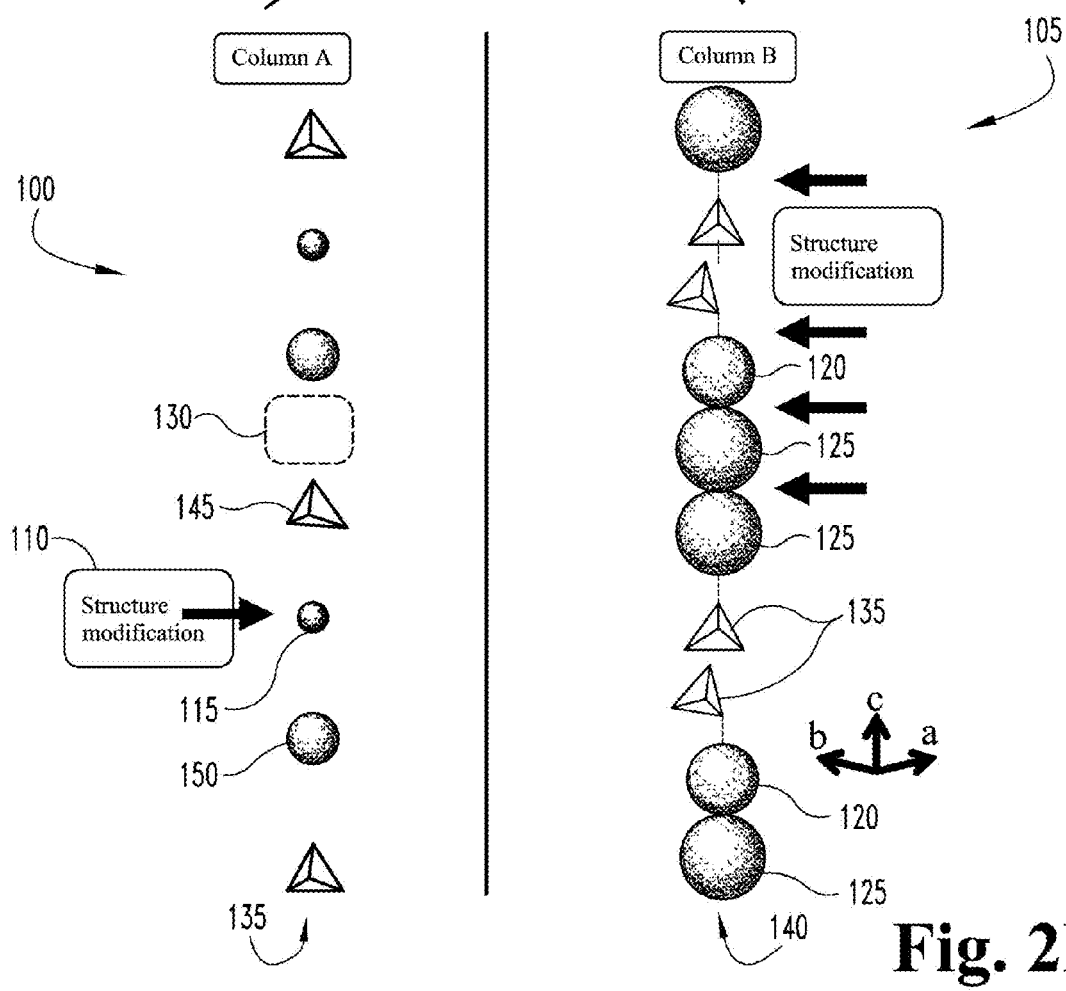

Without being held to any particular theory, it is generally believed that these functionalized moieties 100 may be thought of as distorted calcium phosphate lattices 105 around which fumaric acid 110 has been physically wrapped; the underlying mineral is a distorted tricalcium phosphate matrix having reduced long range order (see FIG. 2). The distorted calcium phosphate materials may be thought of, for convenience, as existing somewhere between β-TCP and amorphous TCP in the crystalline order continuum. The underlying distorted calcium phosphate material is characterized by underbonded calcium oxide clusters ($CaO_3$) 115, calcium oxide clusters ($CaO_7$, $CaO_8$) 120, 125 having shared oxygen vertices and/or edges, and $PO_4$ vacancies 130 in the unit cell crystal lattice. The material's short-range order is similar to that of β-TCP, and may be modeled as a distressed rhombohedral space group R3cH-$C_{3v}$ space group crystal, wherein "A" and "B" columns 135, 140 extend along the C-axis. The A column 135 is characterized by repeating stacks of a $PO_4^{3-}$ tetrahedral 145, a $CaO_6$ calcium oxide cluster 150, and a $CaO_3$ calcium oxide cluster 115. The B column 140 is characterized by repeating stacks of two $CaO_8$ clusters 125, a $CaO_7$ cluster 120, and a pair of $PO_4^{2-}$ tetrahedral 155. The milling and/or grinding process distorts the β-TCP structure enough such that the fumaric acid 110 may be chelated thereto.

The fumaric acid is somewhat uniformly wrapped around the distorted calcium phosphate particles. The fumaric acid is believed to be weakly bonded (such as by hydrogen bond) to the calcium phosphate, such as by chelation or a like bonding mechanism. Further, the fumaric acid is believed to be chelated or coordinated around the CaO clusters, and may be thought of as the promotion of additional defects or intercalation of organic entities into the calcium phosphate crystalline environment, further altering the calcium phosphate lattice structure. Thus, the promotion of defects and/or the intercalation of organic molecules, through chelation or like bonding-coordination into the calcium phosphate lattice creates a hybrid material characterized by increased calcium solubility. Specifically, the presence of fumaric acid yields increased dissolution or solubility of the calcium phosphate skeleton.

The resultant powder is then filtered from the balls and stored, such as in plastic containers. The powder may also be sized, such as through a sieving process, prior to storage. Typically, useful particle size for functionalized moieties is in the range from about 0.1 microns to 20 microns.

After the functionalized moieties are recovered in powder form, they are added to comestibles to yield an improved dental repair product. The solubility of a respective functionalized moiety powder made as described above is a function of the amount of fumaric acid used and the bonding of the fumaric acid to the calcium phosphate. Such comestibles may include candies, mints, gums, lozenges and the like.

It should be noted that in the above example, the fumaric acid is chelated to the distorted calcium phosphate lattice. Thus, it may be possible to sufficiently distort the calcium phosphate lattice via less aggressive grinding and/or milling techniques such that fumaric acid chelation may be achieved. In contrast, if an organic surfactant (such as sodium lauryl sulfate [SLS]) were selected instead of an edible acid, the surfactant would be ionically bonded to the calcium phosphate, and thus the above-described aggressive planetary milling process would typically be employed to sufficiently distress the calcium phosphate lattice to allow ionic bonding of the SLS surfactant.

Comestible Compositions

The present novel technology relates to various comestible compositions, including, for example, candies, confections, chewing gums, lozenges, mints, soluble strips, and the like, as well as to gels, pastes, whitening strips, whitening preparations and other additional dentifrices, while in other embodiments, the present novel technology may be applied to coatings for flosses, brush bristles, and the like. In one particular embodiment, the present novel technology includes a functionalized calcium phosphate material incorporated into a chewing gum comestible. The comestible is a chewing gum having a gum base to which a flavoring agent has been added. The gum base is typically water-insoluble while the flavorant is typically water soluble and selected to release its flavoring agent over a predetermined time period while chewed in the oral environment. A functionalized calcium phosphate material is added to the gum, such as in the form of a coating, and is typically added in an amount between about 0.01 and about 25 weight percent. More typically, the functionalized calcium phosphate material is added in an amount between about 0.1 and about 15 weight percent; even more typically, the functionalized calcium phosphate material is added in an amount between about 0.1 and about 10 weight percent; still more typically, the functionalized calcium phosphate material is added in an amount between about 0.01 and about 5 weight percent; yet more typically, the functionalized calcium phosphate material is added in an amount between about 0.5 and about 5 weight percent. The amount of functionalized calcium phosphate material is selected such that the dissolution/release of calcium into the oral cavity during residence of the gum is sufficient to effect remineralization of the teeth. This amount is a function of the composition of the functionalized calcium phosphate material (i.e., the relative amounts of calcium phosphate to edible acid, the type of edible acid selected, and the mineralogical nature of the starting calcium phosphate material). In other words, the functionalized calcium phosphate material may be tailored for quicker or slower release, and thus greater bioavailability, of its calcium per unit volume of material.

In another embodiment, the functionalized calcium phosphate of the present novel technology is incorporated into a hard candy. The hard candy typically includes a sweet base material, such as sugar and/or corn syrup or, alternately, polyalcohols and high intensity sweetener (such as sucralose or aspartame). The hard candies also typically include flavorings (such as mint oil), fillers (such as starch, magnesium stearate, and the like), and a stabilizer (such as gum acacia). The hard candy may be a medicated lozenge, such as if the flavoring is a strong menthol and/or if other medications are added to the formula. Typically, between about 0.05 and 2 weight percent functionalized calcium phosphate material is added to the hard candy composition to yield a calcium remineralizing hard candy formulation. More typically, between about 0.1 and about 1 weight percent functionalized calcium phosphate material is added; still more typically, between about 0.1 and 0.5 weight percent functionalized calcium phosphate material is added. Further, the functionalized calcium phosphate material is typically formulated to contain about 90 weight percent distressed tricalcium phosphate and about 10 weight percent edible acid, such as fumaric or citric acid, although other ratios such as 95/85/75/50 weight percent distressed calcium phosphate to 5/15/25/50 weight percent edible acid, respectively, may be selected as desired.

In still another embodiment, the functionalized calcium phosphate of the present novel technology is incorporated into a soft, chewy candy. Typically, between about 0.05 and 2 weight percent functionalized calcium phosphate material is added to the soft candy composition to yield a calcium remineralizing hard candy formulation. More typically, between about 0.1 and about 1 weight percent functionalized calcium phosphate material is added; still more typically, between about 0.1 and 0.5 weight percent functionalized calcium phosphate material is added. Further, the functionalized calcium phosphate material is typically formulated to contain about 90 weight percent distressed tricalcium phosphate and about 10 weight percent edible acid, such as fumaric or citric acid, although other ratios such as 95/85/75/50 weight percent distressed calcium phosphate to 5/15/25/50 weight percent edible acid, respectively, may be selected as desired.

Figure 3:
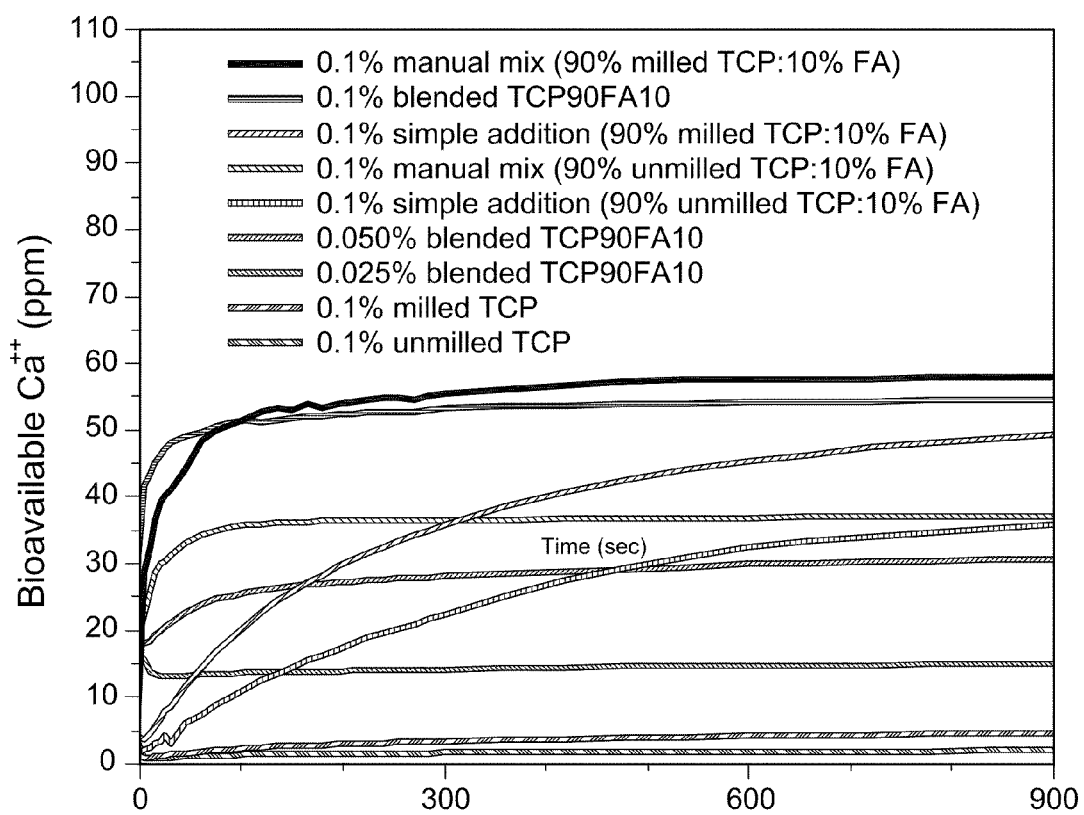
FIG. 3 is a graphic view of calcium solubility isotherms for TCP powders added to solution.

FIG. 3 illustrates the calcium release/bioavailability of various combinations of calcium phosphate and fumaric acid, with the various compositions tabulated below. All compositions in Table 3 include 0.2% citric acid.

TABLE 1

Tabulated data from FIG. 3.

| Group | t = 1 min | t = 2 min | t = 5 min | t = 10 min | t = 15 min |
|---|---|---|---|---|---|
| A | 48.3 | 52.7 | 55.5 | 57.5 | 58.0 |
| B | 49.7 | 51.2 | 53.2 | 54.1 | 54.6 |
| C | 14.2 | 22.5 | 35.8 | 45.3 | 49.5 |
| D | 34.4 | 35.9 | 36.6 | 36.9 | 37.1 |
| E | 7.4 | 12.5 | 22.5 | 32.4 | 35.8 |
| F | 23.8 | 26.1 | 28.1 | 29.9 | 30.6 |
| G | 13.4 | 13.7 | 14.2 | 14.7 | 15.1 |
| H | 1.9 | 2.5 | 3.4 | 4.1 | 4.6 |
| I | 1.2 | 1.4 | 1.7 | 1.9 | 2.0 |

A 0.1 wt. percent manual grinding mix (90% milled TCP: 10% FA)
B 0.1 wt. percent functionalized calcium phosphate (10% FA)
C 0.1 wt. percent blend (90% milled TCP: 10% FA)
D 0.1 wt. percent manual grinding mix (90% unmilled TCP: 10% FA)
E 0.1 wt. percent blend (90% unmilled TCP: 10% FA)
F 0.050 wt. percent functionalized calcium phosphate (10% FA)
G 0.025 wt. percent functionalized calcium phosphate (10% FA)
H 0.1 wt. percent milled TCP
I 0.1 wt. percent unmilled TCP As can be seen in FIG. 3 and table 1, the compositions including fumaric acid were characterized by a greater $Ca^{2+}$ availability over time than those combinations without fumaric acid. Further, the combinations including functionalized calcium phosphate were characterized by a quicker release of calcium ions, with the manually ground compositions falling in the middle and the unmilled compositions having the slowest initial release rates. The compositions with the fastest release rates and that approached their eventual equilibrium solubility the soonest were the functionalized calcium phosphates and the compositions with the overall highest calcium availability were the milled tricalcium phosphates (either planetary milled/functionalized or hand ground) and containing 10 wt. percent fumaric acid.

In any of the above embodiments, other organic acids, such as common flavorant citric acid, may be present as part of the comestible formulation. Typically, comestibles containing both fumaric and citric acid (or other combinations of two or more organic acids) yield increased calcium solubility. Both acids begin to dissolve simultaneously, with the result being a quick dissolution and yield of available calcium for dental remineralization.

Figure 4:
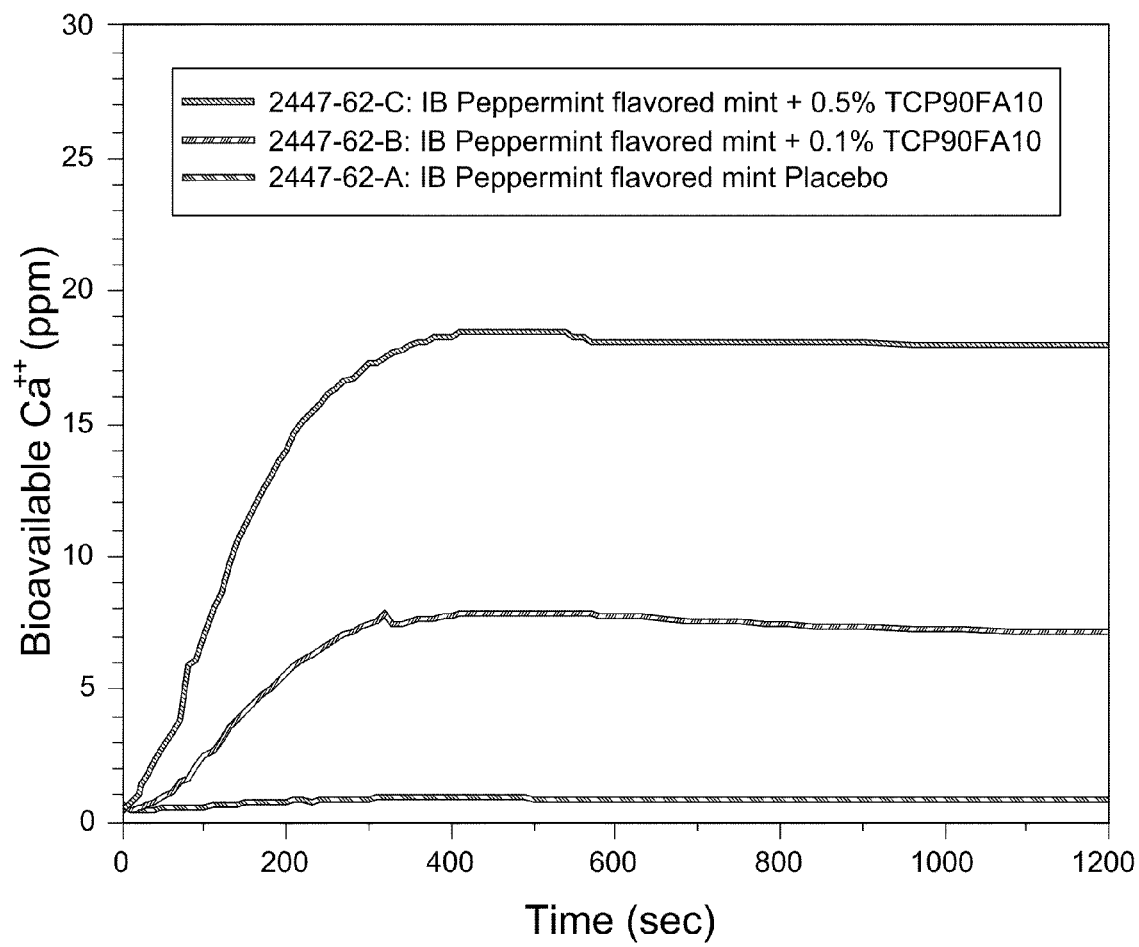
FIG. 4 is a graphic view of calcium solubility isotherms for peppermint flavored mints containing functionalized calcium phosphate additives according to a first embodiment of the present invention.

FIG. 4 illustrates the solubility or bioavailability of $Ca^{2+}$ ions from a relatively hard, pressed tablet formulation to which a 90/10 weight ratio composition of functionalized calcium phosphate was added at zero, 0.1 weight percent and 0.5 weight percent levels. The calcium phosphate was functionalized with 10 weight percent fumaric acid. The original calcium phosphate source material was TCP and the functionalized calcium phosphate moiety material was prepared as described above with a 2 hour planetary ball milling time.

Figure 5:
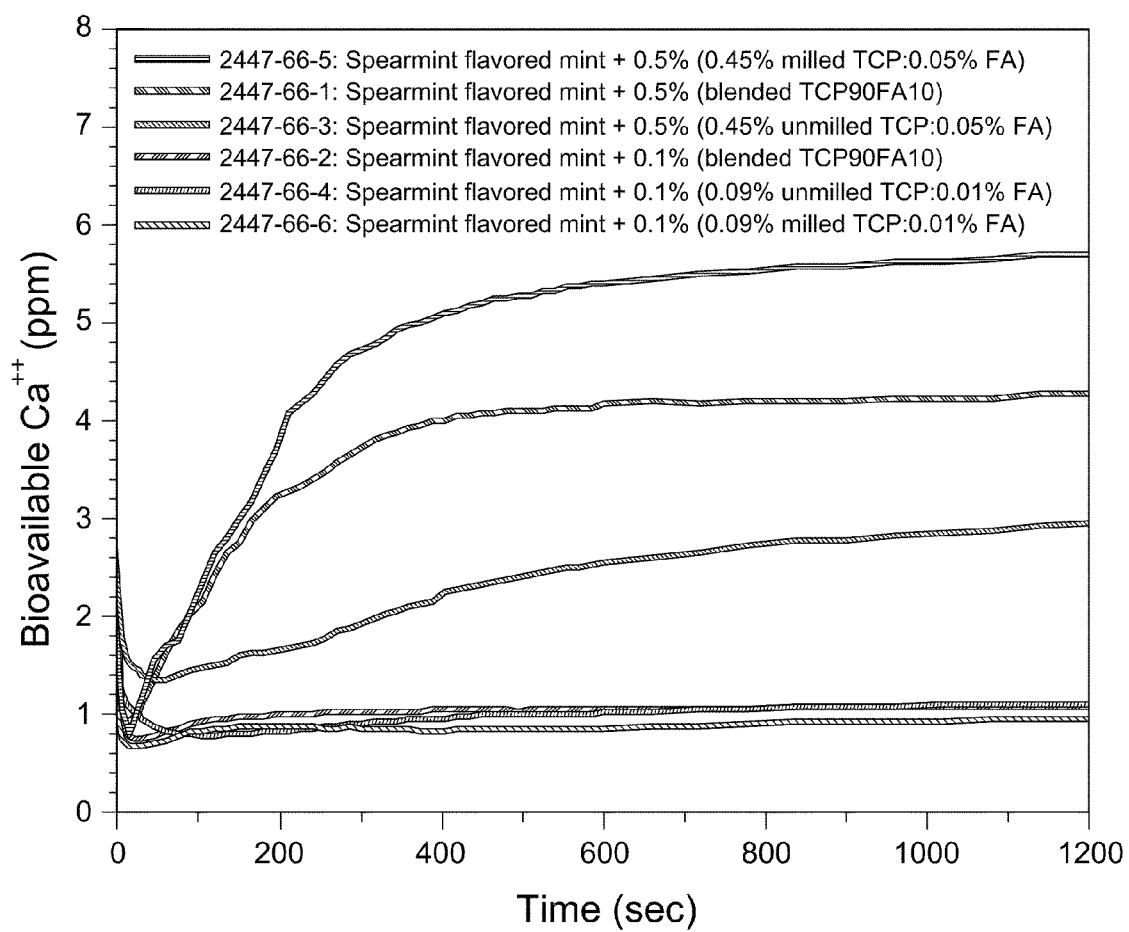
FIG. 5 is a graphic view of calcium solubility isotherms for spearmint flavored mints containing functionalized calcium phosphate additives according to a first embodiment of the present invention.
Figure 6:
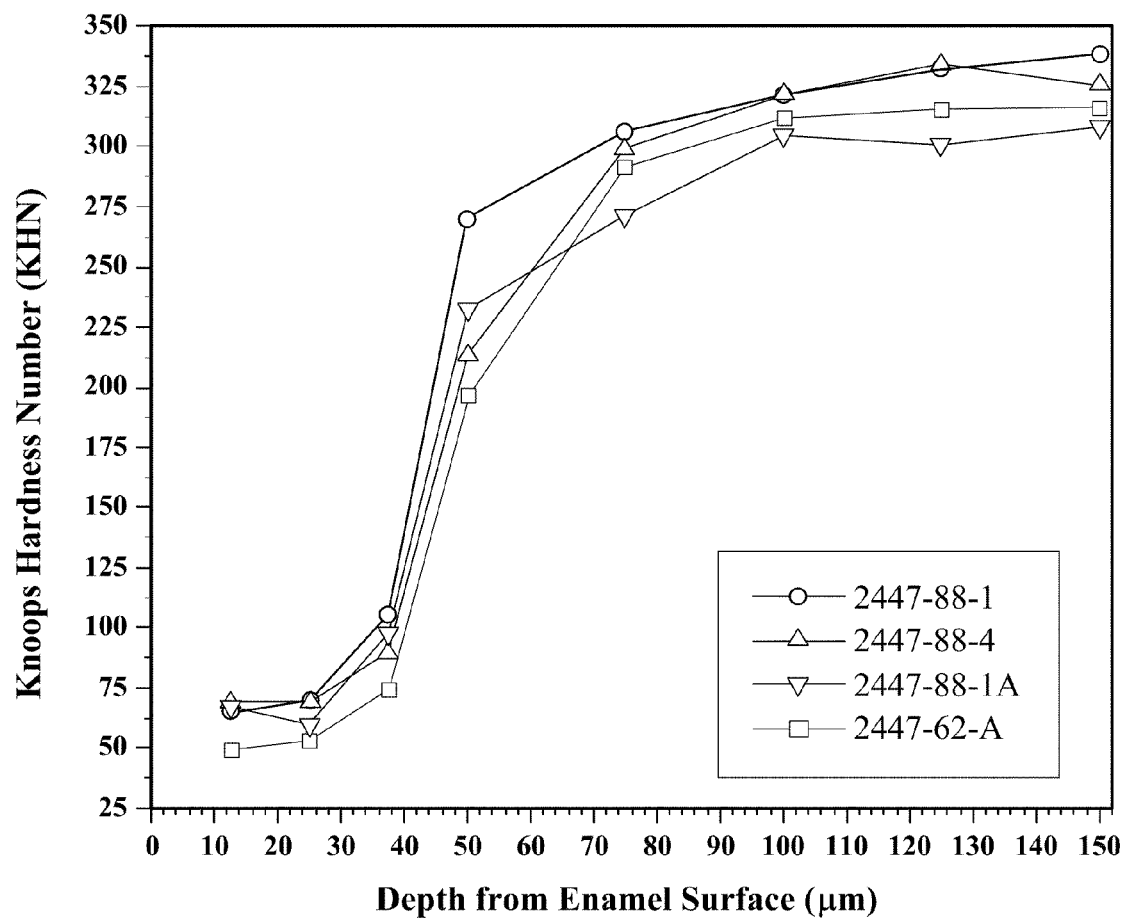
FIG. 6 is a plot of the effects on subsurface dental remineralization in terms of KHN over depth for dentition treated with functionalized calcium phosphate additives according to a first embodiment of the present invention.

FIG. 5 and table 2 similarly illustrate the solubility or bioavailability of $Ca^{2+}$ ions from a series of hard mints, identical but for the relative amounts and formats of the calcium phosphate additives.

TABLE 2

| Group | Mean (averaged over three individual runs) Bioavailable $Ca^{++}$/ppm @ | | | | | |
|---|---|---|---|---|---|---|
| | t = 1 min | t = 2 min | t = 5 min | t = 10 min | t = 15 min | t = 20 min |
| 2447-62-C | 3.3 | 8.7 | 17.3 | 18.1 | 18.1 | 18.0 |
| 2447-62-B | 1.2 | 3.1 | 7.5 | 7.7 | 7.3 | 7.2 |
| 2447-62-A | 0.5 | 0.6 | 0.9 | 0.9 | 0.8 | 0.8 |
| 2447-66-5 | 1.7 | 2.6 | 4.7 | 5.4 | 5.6 | 5.7 |
| 2447-66-1 | 1.6 | 2.4 | 3.7 | 4.2 | 4.2 | 4.3 |
| 2447-66-3 | 1.4 | 1.5 | 1.9 | 2.6 | 2.8 | 2.9 |
| 2447-66-2 | 0.8 | 1.0 | 1.0 | 1.1 | 1.1 | 1.1 |
| 2447-66-4 | 0.8 | 0.8 | 0.9 | 1.0 | 1.1 | 1.1 |
| 2447-66-6 | 0.7 | 0.9 | 0.9 | 0.9 | 0.9 | 0.9 | where
2447-62-A peppermint flavored mint standard
2447-62-B peppermint flavored mint + 0.1 wt. % functionalized calcium phosphate (10% fumaric acid)
2447-62-C peppermint flavored mint + 0.5 wt. % functionalized calcium phosphate (10% fumaric acid)
2447-66-1 spearmint flavored mint + 0.5 wt. % functionalized calcium phosphate (10% fumaric acid)
2447-66-2 spearmint flavored mint + 0.1 wt. % functionalized calcium phosphate (10% fumaric acid)
2447-66-3 spearmint flavored mint + 0.5 wt. % blend (90% unmilled TCP: 10% fumaric acid)
2447-66-4 spearmint flavored mint + 0.1 wt. % blend (90% unmilled TCP: 10% fumaric acid)
2447-66-5 spearmint flavored mint + 0.5 wt. % blend (90% milled TCP: 10% fumaric acid)
2447-66-6 spearmint flavored mint + 0.1 wt. % blend (90% milled TCP: 10% fumaric acid)

In addition to the 90/10 weight ratio compositions of functionalized calcium phosphate added at 0.1 weight percent and 0.5 weight percent levels, 90/10 weight ratio blends of unfunctionalized but milled TCP mixed with fumaric acid were added at 0.1 weight percent and 0.5 weight percent levels and 90/10 weight ratio blends of unfunctionalized and unmilled TCP mixed with fumaric acid were added at 0.1 weight percent and 0.5 weight percent levels to yield six different mint compositions.

Remineralization Studies

The effect of functionalized calcium phosphate material on tooth remineralization was investigated. In one study, the potential efficacy of a functionalized calcium phosphate powder (made from 90 weight percent TCP precursor material with the remainder fumaric acid and high-energy milled as described above in a planetary bill mill for 2 hours) was studied in remineralizing white-spot enamel lesions via a sugarless chewing gum format. To better emulate 'real' chewing gum scenarios, sticks of a sugar free chewing gum, with and without added functionalized calcium phosphate additive, were chewed by human subjects with the resulting saliva generated during the event collected and used as the bovine dental 'treatment'. When present, the functionalized calcium phosphate additive was added as a coating, such as dusted onto the chewing gum.

Bovine enamel specimens (3 mm) were ground and polished using standard methods. Three groups (N=10) of specimens were prepared for this study. Artificial lesions were formed in the enamel specimens by immersion into a carbopol-lactic acid solution which had been saturated with hydroxyapatite and adjusted to pH 5.0 at 37° C. Three treatment groups were in the study:
Group 1: DI Water
Group 2: Sugar free gum
Group 3: Sugar free gum+0.5% FA functionalized calcium phosphate Subjects chewed gum and expectorated saliva into cups which were then used as the treatments. Four 20-minute treatment periods and three 20-minute acid challenge periods were given daily with the remainder of the time the specimens were immersed in artificial saliva. Enamel specimens (N=10 for each group) were cycled for 5 days in artificial saliva (pH=7), in a carbopol-lactic acid challenge (pH=5), and in expectorated saliva (pH between 7 and 8). After 5 days specimens were analyzed for surface microhardness as shown below in Table 3. New enamel specimens were then used and cycled for another 5 days with subjects alternating treatments—results shown in Table 4.

TABLE 3

Remineralization determined via Vickers surface microhardness after 5 days of pH cycling. Superscripts indicate significant differences ($p < 0.05$, one-way ANOVA, SNK method), where 1 < 2 < 3.

| Group | Mean ΔVHN ± SEM |
|---|---|
| [1]DI Water | 6.4 ± 0.6 |
| [2]Sugarfree gum | 9.5 ± 1.3 |
| [3]Sugarfree gum + 0.5% FA functionalized calcium phosphate | 16.0 ± 1.0 |

TABLE 4

Remineralization determined via Vickers surface microhardness after 5 days of pH cycling. Superscripts indicate significant differences ($p < 0.05$, one-way ANOVA, SNK method), where 1 < 2 < 3.

| Group | Mean ΔVHN ± SEM |
|---|---|
| [1]DI Water | 3.4 ± 0.9 |
| [2]Sugarfree gum | 6.5 ± 0.5 |
| [3]Sugarfree gum + 0.5% FA functionalized calcium phosphate | 10.2 ± 0.9 |

The addition of the functionalized calcium phosphate material provided an additional 62% remineralization over the reference standards.

A second study was conducted to evaluate the efficacy of the fumaric acid functionalized calcium phosphate material (made from 90 weight percent TCP precursor material with the remainder fumaric acid and high-energy milled as described above in a planetary bill mill for 2 hours) as compared to a commercially available non-functionalized calcium phosphate remineralization material, RECALDENT® (RECALDENT is a registered trademark of Cadbury Enterprises PTE LTD Limited Company, Singapore, 346 Jalan Boon Lay Jurong Singapore 61952) in remineralizing white-spot enamel lesions. Again, to better emulate 'real' chewing gum scenarios, sticks of a sugarless chewing gum and TRIDENT XTRA CARE® with RECALDENT® chewing gums were chewed by human subjects, with the saliva generated during the event used as the 'treatment' (TRIDENT XTRA CARE is a registered trademark of Cadbury Adams LLC, 389 Interpace Parkway, Parsippany, N.J. 07054).

Bovine enamel specimens (3 mm) were ground and polished using standard methods. Three groups (N=10) of specimens were prepared for this study. Artificial lesions were formed in the enamel specimens by immersion into a carbopol-lactic acid solution which had been saturated with hydroxyapatite and adjusted to pH 5.0 at 37° C. Three treatments groups were in the study:

Group 1: DI Water
Group 2: Sugar free gum+0.1% FA functionalized calcium phosphate system
Group 3: Trident XtraCare Subjects chewed gum and expectorated saliva into cups which were then used as the treatments. Four 20-minute treatment periods and three 20-minute acid challenge periods were given daily; during the remainder of the time the specimens were immersed in artificial saliva. Enamel specimens (N=10 for each group) 'cycled' for 4 days in artificial saliva (pH=7), in a carbopol-lactic acid challenge (pH=5), and in expectorated saliva (pH between 7 and 8). After 4 days specimens were analyzed for surface microhardness as shown in Table 5.

TABLE 5

Remineralization determined via Vickers surface microhardness after 5 days of pH cycling. Superscripts indicate significant differences (p < 0.05, one-way ANOVA, SNK method), where 1 < 2 < 3.

| Group | Mean ΔVHN ± SEM |
|---|---|
| [1]DI Water | 1.7 ± 0.4 |
| [3]Sugarfree gum + 0.1% TCP-FA | 10.0 ± 0.8 |
| [2]Trident Xtra Care | 3.8 ± 0.7 |

The efficacy of sugar free gum+0.1% FA functionalized calcium phosphate provided an additional 162% remineralization improvement relative to Trident Xtra Care sugar free gum incorporating the Recaldent® technology.

In another study, the efficacy of fumaric acid functionalized calcium phosphate (made from 90 weight percent TCP precursor material with the remainder fumaric acid and high-energy milled as described above in a planetary bill mill for 2 hours) to remineralize white-spot enamel lesions and whiten enamel was studied in a sugarless chewing gum format. To better emulate 'real' chewing gum scenarios, sticks of a sugar free chewing gum were chewed by human subjects, with the resulting saliva generated during the event used as the 'treatment'.

Bovine enamel specimens (3 mm) were ground and polished using standard methods. Three groups (N=10) of specimens were prepared for this study. Artificial lesions were formed in the enamel specimens by immersion into a carbopol-lactic acid solution which had been saturated with hydroxyapatite and adjusted to pH 5.0 at 37° C. The treatment groups included Group 1: Distilled water (negative control) treatment;
Group 2: Sugar free chewing gum (positive control); and
Group 3: Sugar free chewing gum+0.1% FA functionalized calcium phosphate.

Test subjects chewed gum and expectorated saliva into cups which were then used as the treatments. Four 20-minute treatment periods and three 20-minute acid challenge periods were given daily with the remainder of the time the specimens were immersed in artificial saliva. Enamel specimens (N=10 for each group) 'cycled' for 5 days in artificial saliva (pH=7), in a carbopol-lactic acid challenge (pH=5), and in expectorated saliva (pH between 7 and 8). After 5 days specimens were analyzed for surface microhardness as shown in Table 6. Using a colorimeter, specimens were then analyzed for color based on the Commission Internationale de l'Eclairage (CIE) Lab color space b* axis, which represents the yellowness (positive values, undesirable) or blueness (negative values, desirable), as shown in Table 6.

TABLE 6

Remineralization determined via Vickers surface microhardness after 5 days of pH cycling. Superscripts indicate significant differences (p < 0.05, one-way ANOVA, SNK method), where 1 < 2 < 3.

| Group | Mean ΔVHN ± SEM | b* |
|---|---|---|
| DI Water | 3.1 ± 0.9[1] | −15.1 ± 0.5[1] |
| Sugar free gum | 6.8 ± 1.4[2] | −15.5 ± 0.9[1] |
| Sugar free gum + 0.1% FA functionalized calcium phosphate | 9.8 ± 1.3[3] | −16.7 ± 1.4[2] |

Efficacy of sugar free gum+0.1% FA functionalized calcium phosphate provided a statistically significant boost (44.1%) in remineralization relative to the control sugar free gum in this short-term study. The color of the specimens treated with the sugar free gum+0.1% FA functionalized calcium phosphate was found to be statistically bluer (i.e. less yellow, more white) relative to the control sugar free gum (~8% whiter) in this short-term study.

Another study was done, investigating the remineralization efficacy of the mint compositions detailed above in Table 2. The cyclic treatment procedure consisted of three 20-minute white-spot (carbopol-lactic acid, pH=5.0) challenges and five 4-minute treatment periods. Prior to treatment the mints were dissolved for 7 minutes via magnetic agitation at 300 rpm in 15 mL distilled water, which will then be the treatment solution. The cycle was repeated for 5 days, at which point interim measurements were made. The cycle was then continued for another 5 days (10 days total). The treatment schedule was:

a. Acid challenge (20 min)
b. Treatment (4 min)
c. Artificial Saliva (1.5 hours)
d. Treatment (4 min)
e. Artificial Saliva (1.5 hours)
f. Acid challenge (20 min)
g. Treatment (4 min)
h. Artificial Saliva (1.5 hours)
i. Treatment (4 min)
j. Artificial Salivat (1.5 hours)
k. Acid challenge (20 min)
l. Treatment (4 min)
m. Artificial Saliva (overnight)
‡Fresh saliva changed.

The pH Cycling Results are as Follows:

TABLE 7

Change in Vicker microhardness (ΔVHN) and blueness (Δb) relative to baseline after 5[a] days and 10[b] days of cycling among the mint groups (N = 10). The more negative a Δb value, the 'whiter' the surface.
Peppermint flavored mint formats

| Group | ΔVHN, Mean ± SEM[a] | ΔVHN, Mean ± SEM[b] | Δb, Mean ± SEM[b] |
|---|---|---|---|
| 2447-62-A | 5.3 ± 1.1[1] | 5.1 ± 1.0[1] | −0.01 ± 0.25 |
| 2447-62-B | 8.7 ± 1.0[2] | 9.1 ± 1.3[2] | −0.34 ± 0.23 |
| 2447-62-C | 9.1 ± 1.9[2] | 8.8 ± 1.5[2] | −0.76 ± 0.22 |

Statistical differences were observed for the FA functionalized calcium phosphate and placebo standards. Composition 2447-62-B produced statistically equivalent (multiple t-test comparisons at the 95% confidence level) remineralization relative to composition 2447-62-C after 5 and 10 days of cycling. Composition 2447-62-B produced about 33% more 'whitening' relative to composition 2447-62-A (placebo). Composition 2447-62-C provided about 75% more 'whitening'. The near doubling of the whitening benefits from composition 2447-62-C compares well with the nearly 2.5× more bioavailable calcium released relative to composition 2447-62-B. These data indicate remineralization is independent of high calcium bioavailability, so a recommended dose level should be based on efficacy, not bioavailability. These data indicate that a relatively higher calcium bioavailability has a pronounced effect on whitening.

Table 8 below contains the results for the spearmint-flavored mint formats:

TABLE 8

Change in Vickers microhardness (ΔVHN) and blueness (Δb) relative to baseline after 5[a] days and 10[b] days of cycling among the mint groups (N = 10). The more negative a Δb value, the 'whiter' the surface.

| Group | ΔVHN, Mean ± SEM[a] | ΔVHN, Mean ± SEM[b] | Δb, Mean ± SEM[b] |
|---|---|---|---|
| 2447-66-1 | 7.4 ± 1.3 | 12.3 ± 1.4 | −0.12 ± 0.20 |
| 2447-66-2 | 6.5 ± 1.3 | 14.6 ± 1.2 | −0.19 ± 0.18 |
| 2447-66-3 | 4.4 ± 0.8 | 10.7 ± 0.9 | 0.12 ± 0.20 |
| 2447-66-4 | 5.1 ± 1.3 | 12.5 ± 2.1 | −0.06 ± 0.13 |
| 2447-66-5 | 4.7 ± 0.8 | 12.5 ± 1.0 | 0.20 ± 0.19 |
| 2447-66-6 | 9.0 ± 1.5 | 13.3 ± 1.9 | 0.08 ± 0.21 |

Hardness differences were observed after 5 and 10 days of pH cycling, with directional superiority indicating that the samples with functionalized calcium phosphate tended to experience greater remineralization than did the other samples.

In general, unmilled TCP-FA mint formats did not remineralize as well as milled TCP-FA, which suggests the importance of milled TCP. In terms of whitening benefits, the blended fumaric acid functionalized calcium phosphate additives (Groups 1 & 2) provided the best benefits relative to unmilled TCP (Groups 3 & 4) and milled TCP (Groups 5 & 6). In the current spearmint flavored mint format, these data indicate that blended TCP90FA10 gave rise to a pronounced effect on whitening. For the current mint formats, these data suggest the low levels of bioavailable calcium obscures differences among the groups in terms of remineralization benefits; however, significantly better whitening benefits are observed for mints comprising fumaric acid functionalized calcium phosphate additives.

Typically, functionalized moieties (such as fumaric acid functionalized calcium phosphate additives compounds), are added to comestibles in concentrations of about 0.01 wt. % to about 1.0 wt. %, and more typically in concentrations of between about 0.05 wt. % and about 0.5 wt. %. The functionalized moieties may be added primarily as a surface treatment or distributed substantially throughout the comestible, either uniformly or non-uniformly.

In a subsequent study, the effects of differences in milling of β-TCP in the presence or absence of fumaric acid on the remineralization properties of the resultant milled material were investigated. A 10-day remin/demin cycling model was instituted in order to identify differences among comestible delivery platforms (in this study, mints) having no TCP-FA (control sample 2447-62-A), milled TCP-FA (test sample 2447-88-1) and milled TCP without fumaric acid (test sample 2447-88-4). The dentition substrate specimens were again bovine.

Microhardness measurements were conducted as described above. The (mean VHN±Std Dev) results of the surface microhardness results were the following:
  2447-62-A: 9.7±2.3 VHN[a]
  2447-88-1: 16.4±4.8 VHN[b]
  2447-88-4: 16.5±8.3 VHN[b]
Samples 2447-88-1 and 2447-88-4 were not found to be statistically independent in terms of surface microhardness (which extends to an enamel depth of about 10 microns). Relatively high standard deviations (such as that for mint 2447-88-4) typically occur for unmilled or milled β-TCP; this likely results from an unstabilized remineralization process that results in both hard and soft mineral formation that ultimately influence enamel strength when subjected in a remin/demin study manifesting multiple acid challenges.

Whitening effects were also observed and were most pronounced for treatment systems 2447-88-1 and 2447-88-4 (which were found to be almost equivalent to each other) over the standard control sample by a significant difference of about −1. These results are consistent with the prior studies, as significant bulk effects were observed for the TCP-FA material as previously demonstrated. These results are shown in FIGS. 6 and 7A-7D. For reference, it should be noted that the Vickers Hardness Number (VHN) generated on the surface of the enamel specimen subjected to the remin/demin cycling environment as described above generally penetrates down to a depth of about 10 μm. Thus, the mechanism of sub-surface remineralization is of interest, especially in light of the whitening results and similar surface microhardness results. The microhardness data represents cross-sectional results for the three specimen groups from the 10-day cycling study of the enamel specimens, with each specimen group having 10 individual specimens.

Figure 7A:
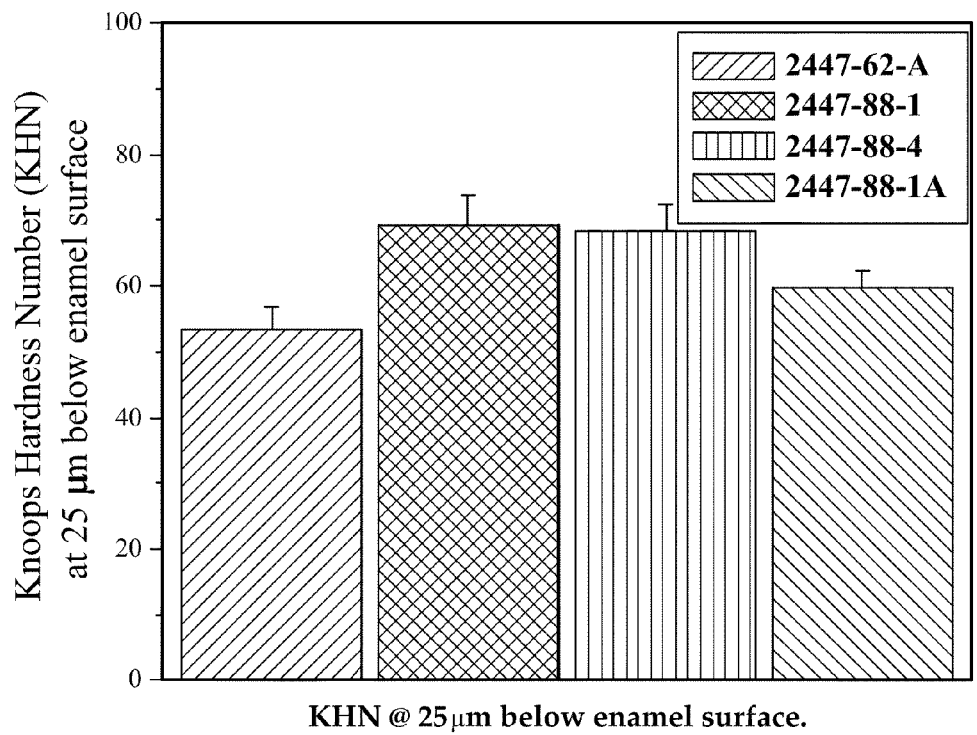
FIG. 7A is a graphic view of subsurface dental remineralization effects at a depth of 25 μm for functionalized calcium phosphate additives according FIG. 6.

Referring specifically to FIG. 7A, the KHN of dental specimens at a depth of 25 μm below the enamel surface is plotted for dentition treated with systems having no TCP-FA (control sample 2447-62-A), milled TCP-FA (test sample 2447-88-1), milled TCP without fumaric acid (test sample 2447-88-4), and native TCP with fumaric acid (test sample 2447-88-1A). The depth of 25 μm marks the initial depth into the non-cavitated, early caries (i.e. the so-called white-spot) lesion. The white-spot lesion is typically characterized by extending between 15 and 75 μm below the enamel surface, however, some lesions can be shallower or deeper depending on the nature of the acid attack and the properties of enamel. Here, systems 2447-88-1 and 2447-4 provide the most significant remineralization over systems 2447-62-A and 2447-88-1A, which are statistically similar.

Figure 7B:
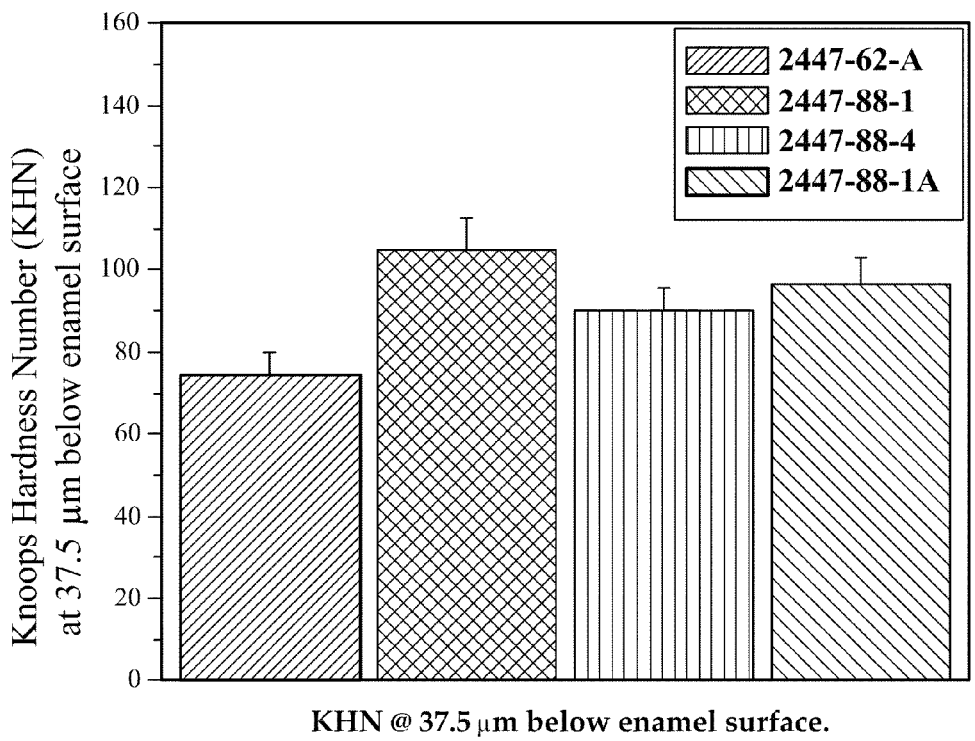
FIG. 7B is a graphic view of subsurface dental remineralization effects at a depth of 37.5 μm for functionalized calcium phosphate additives according FIG. 6.

Referring to FIG. 7B, the KHN of dentition specimens was measured deeper within the white-spot lesions at a depth of 37.5 µm below the enamel surface. Significant differences among treatment systems are observed, with system 2447-88-1 providing the most significant remineralization. This indicates that the functionalized form of tricalcium phosphate leads to substantial remineralization in the body of the early caries lesion relative to native or milled tricalcium phosphate, whether or not fumaric acid is present. The 2447-88-4 and 2447-88-1a systems are not statistically different in their ability to remineralize the white-spot lesion, but are both superior to the 2447-62-A system.

Figure 7C:
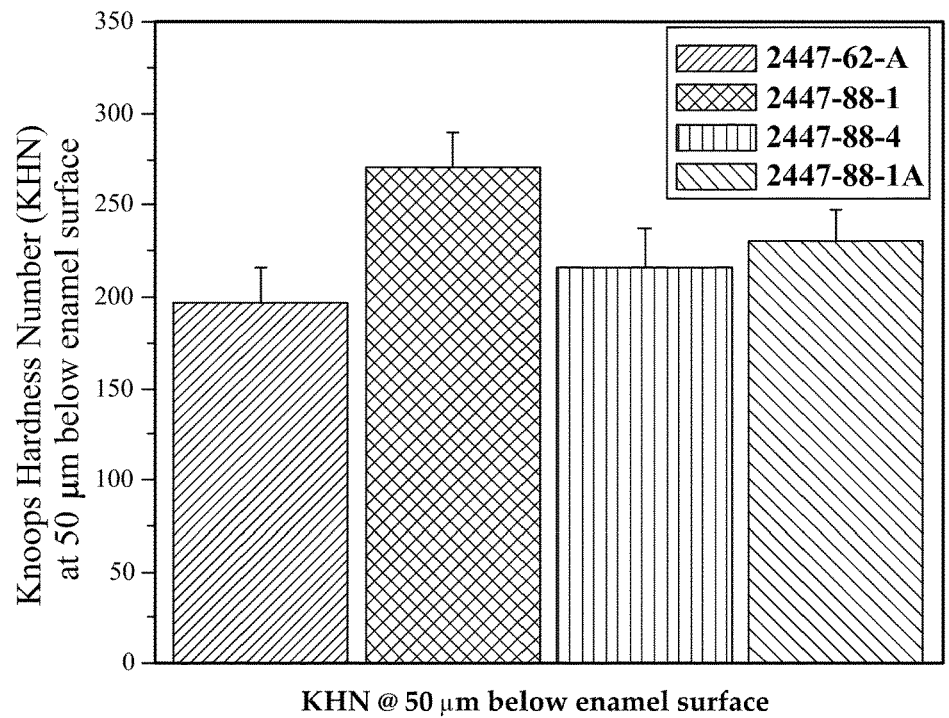
FIG. 7C is a graphic view of subsurface dental remineralization effects at a depth of 50 μm for functionalized calcium phosphate additives according FIG. 6.

Referring to FIG. 7C, KHN measurements are given for the 4 systems at depths of 50 µm below the enamel surface and still within the body of the white-spot lesion. Significant differences among treatment systems are still observed. Here, system 2447-88-1 provides the greatest statistical remineralization potential, indicating that the functionalized form of tricalcium phosphate with fumaric acid leads to substantial remineralization in the body of the early caries lesion relative to native or milled tricalcium phosphate, whether the native or milled tricalcium phosphate is in the presence or absence of fumaric acid. The remaining three systems are not statistically different in their ability to remineralize the white-spot lesion.

Figure 7D:
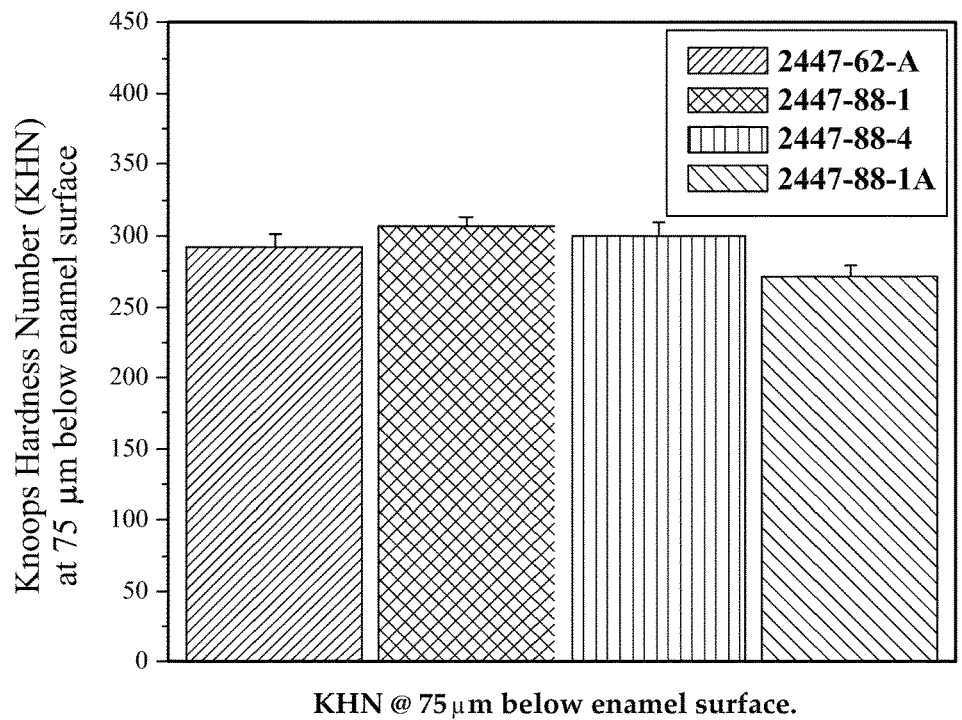
FIG. 7D is a graphic view of subsurface dental remineralization effects at a depth of 75 μm for functionalized calcium phosphate additives according FIG. 6.

Referring to FIG. 7D, KHN measurements of enamel taken at depths of 75 microns are presented. The depth of 75 µm below the enamel surface marks the endpoint of the white-spot enamel lesion and subsequent interfacing with the underlying sound enamel in the dentition samples studied herein. Only subtle differences in KHN measured hardness are observed among dentition treated with systems 2447-62-A, 2447-88-1, and 2447-88-4; however, dentition treated with 2447-88-1A yields statistically softer dentition, indicating that this formulation does not prevent mineral leaching from the underlying sound enamel caused by repeated exposure to acidic events.

All specimens were cross-sectioned and the longitudinal Knoops Hardness Number (KHN) was obtained for one-half of the specimen at increments from the enamel surface at 12.5, 25, 37.5, 50, 75, 100, 125, and 150 µm. This was done in triplicate per specimen resulting in 30 measurements (3 measurement lanes for each of the N=10 specimens) at each depth. A 10 gram-force loading level was used at the first four measurements, while a 50 gram-force load was used for the remaining four measurements. All measurements were converted from indent length to KHN, since the square root of KHN can be obtained and correlates directly with volume percent mineral.

Table 9 below summarizes the pH data collected for the specimens.

TABLE 9

Average pH values as a function of mint dissolution
in distilled water (1:9 dilution) at 37.8° C.

Measured pH as a function of mint dissolution

| Mint | 15 sec | 30 sec | 45 sec | 1 min | 2 min | 3 min | 4 min | 5 min | 6 min | 7 min | 8 min |
|---|---|---|---|---|---|---|---|---|---|---|---|
| 2447-88-1 | 3.73 | 3.67 | 3.58 | 3.65 | 3.71 | 3.71 | 3.76 | 3.80 | 3.80 | 3.83 | 3.85 |
| 2447-88-1A | 4.08 | 4.09 | 4.13 | 4.11 | 4.13 | 4.18 | 4.17 | 4.20 | 4.23 | 4.24 | 4.24 |
| 2447-88-4 | 3.82 | 3.82 | 3.84 | 3.87 | 3.94 | 4.01 | 4.04 | 4.10 | 4.11 | 4.07 | 4.07 |
| 2447-88-4A | 3.87 | 3.75 | 3.68 | 3.71 | 3.86 | 3.89 | 3.93 | 3.95 | 3.96 | 3.96 | 3.97 |

As can be seen in the Table 9 data, the pH marginally varies during mint dissolution (no more than 0.15 pH units for specimen 2447-88-1 comprising the TCP-FA blend and no more than 0.24 pH units for specimen 2447-88-1A) through 8 minutes of dissolution.

In summary, we note that specimen group 2447-88-1 appears to give rise to the deepest mineral penetration into the sub-surface (i.e. white-spot) lesion, and is especially apparent in the range between 40 and 80 µm, to promote bulk remineralization. Within this range, there is a significant difference in microhardness relative to specimen group 2447-88-4. It is likely that the functional attachment of fumaric acid to β-TCP during the milling process is contributes to retaining the TCP-FA coordination; in turn, this coordination likely stabilizes remineralization events and provides more stronger, more acid-resistant mineral phases that do not demineralize as much as the control specimen group or specimen group 2447-88-4 when exposed to an acid challenge. Further, the TCP-FA material likely prevents demineralization from within the enamel specimen during the acid challenges in the remin/demin cycling model. Without a good 'barrier' to demineralization, mineral will leach from within the body of the specimen (not just the lesion) to promote softening.

Table 10 presents data for the specimen groups of the 10-day remin/demin model:

TABLE 10

| | |
|---|---|
| 2447-62-A: | control group mint without calcium phosphate |
| 2447-88-1: | mint containing the functionalized form of TCP with fumaric acid |
| 2447-88-1A: | mint containing native β-TCP and fumaric acid |
| 2447-88-4: | mint containing milled β-TCP but without fumaric acid |
| 2447-88-4A: | mint containing native β-TCP but without fumaric acid |

Table 11 presented below is a summary of mints and the corresponding surface microhardness (mean VHN+/−std. dev.) for mints examined in a 10-day remin/demin cycling study. The data that show mints 2447-91-3 and 2447-91-1 had a hydrated form of beta tricalcium phosphate and did not fare well against the functionalized mint in terms of remineralization efficacy. It should be noted that although the surface hardness for groups 2, 3, and 4 below were essentially the same, the cross-sectional data in FIG. 6 clearly shows a subsurface effect for mint 2447-88-1 comprising the functionalized TCP-FA material.

TABLE 11

| | |
|---|---|
| 2447-62-A: | control standard mint without calcium phosphate; VHN after remin/demin cycling model: 14.2 +/− 1.4 |
| 2447-88-1: | mint containing functionalized TCP with fumaric acid; VHN after remin/demin cycling model: 22.2 +/− 4.8 |
| 2447-88-1A: | mint containing native β-TCP and fumaric acid; VHN after remin/demin cycling model: 20.9 +/− 7.2 |
| 2447-88-4A: | mint containing native β-TCP but without fumaric acid; VHN after remin/demin cycling model: 22.1 +/− 7.5 |
| 2447-91-3: | mint containing milled hydrated TCP and without fumaric acid; VHN after remin/demin cycling model: 13.4 +/− 4.1 |
| 2447-91-1: | mint containing native hydrated TCP and without fumaric acid; VHN after remin/demin cycling model: 11.9 +/− 3.4 |

Table 12 below summarizes the whitening benefits observed of the TCP-FA system, with the corresponding whiteness from the specimens examined above in the same 10-day remin/demin cycling study. The more negative, or 'bluer', the number, the more 'whiter' the treated dentition. Mint 2447-88-1 comprising the functionalized TCP-FA material was numerically and/or significantly greater than the other groups observed.

TABLE 12

| | |
|---|---|
| 2447-62-A: | control standard mint without calcium phosphate; whiteness: −3.9 +/− 1.5 |
| 2447-88-1: | mint containing functionalized TCP-FA; whiteness: −4.9 +/− 1.1 |
| 2447-88-1A: | mint containing native β-TCP and fumaric acid; whiteness: −4.2 +/− 1.2 |
| 2447-88-4A: | mint containing native β-TCP but without fumaric acid; whiteness: −4.2 +/− 1.2 |
| 2447-91-3: | mint containing milled hydrated TCP and without fumaric acid; whiteness: −3.8 +/− 0.8 |
| 2447-91-1: | mint containing native hydrated TCP and without fumaric acid; whiteness: −4.0 +/− 1.6 |

While the invention has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the invention are desired to be protected.

What is claimed is:

1. A method for remineralization of dentition, comprising:
   mechanochemically distressing the lattice structure of a first predetermined amount of beta tricalcium phosphate in a high-energy planetary ball mill to yield a quantity of distressed calcium phosphate material;
   incorporating the distressed calcium phosphate material into a comestible to yield a calcium phosphate delivery platform;
   introducing the calcium phosphate delivery platform to dentition in an oral environment; and
   remineralizing dentition;
   wherein remineralization occurs at a dentition depth of at least 40 microns below the surface.

2. The method of claim 1 wherein the comestible is selected from the group including candies, mints, gums, and lozenges.

3. The method of claim 1 wherein the distressed calcium phosphate material is added to the comestible in a concentration of between about 0.01 and about 5 weight percent.

4. The method of claim 1 wherein remineralization occurs at a dentition depth of at least 40 microns below the surface.

5. The method of claim 1 wherein remineralization occurs at a dentition depth of at least 70 microns below the surface.

6. The method of claim 1 wherein remineralization occurs at depths of about 50 microns and is accompanied by an increase in Knoops hardness to at least about 250.

7. The method of claim 1 wherein the dentition includes subsurface enamel lesions occurring at depths of more than about 10 microns and wherein the subsurface enamel lesions are substantially remineralized.

8. The method of claim 1 wherein the distressed calcium phosphate material is unhydrated.

9. A method for remineralizing teeth, comprising:
   distressing the lattice structure of a first predetermined amount of beta tricalcium phosphate to yield a distorted tricalcium phosphate material having increased solubility and bioavailablity;
   incorporating the distorted tricalcium phosphate material into a comestible to yield a calcium phosphate delivery platform;
   introducing the calcium phosphate delivery platform to dentition in an oral environment; and
   remineralizing dentition;
   wherein remineralization occurs at a dentition depth of at least 10 microns below the surface;
   wherein the lattice structure is distressed by high energy planetary ball milling; and
   wherein remineralization occurs at depths of about 50 microns and is accompanied by an increase in Knoops hardness to at least about 250.

10. The method of claim 1 wherein the bioavailability of the distressed calcium phosphate material is at least twice that of beta tricalcium phosphate.

11. A method for dentition remineralization, comprising:
    physically distressing the lattice structure of a first predetermined amount of beta tricalcium phosphate in a high-energy planetary ball milling operation to yield a crystallographically different distressed calcium phosphate material;
    introducing the distressed calcium phosphate material into an oral environment;
    and
    remineralizing dentition to a depth of at least 70 microns.

* * * * *